United States Patent [19]

Nakaya et al.

[11] Patent Number: 5,554,593

[45] Date of Patent: Sep. 10, 1996

[54] THERAPEUTIC AGENT FOR THREATENED ABORTION

[75] Inventors: Takayoshi Nakaya, Nagoya; Yayoi Kajiwara, Kawasaki, both of Japan

[73] Assignee: Hoechst Japan Limited, Tokyo, Japan

[21] Appl. No.: 364,077

[22] Filed: Dec. 23, 1994

Related U.S. Application Data

[63] Continuation of Ser. No. 26,010, Mar. 4, 1993, abandoned.

[30] Foreign Application Priority Data

Jun. 6, 1992 [JP] Japan .................................. 4-449353

[51] Int. Cl.⁶ ..................... A61K 35/16; A61K 35/50; A61K 38/43; A61K 26/00
[52] U.S. Cl. ..................... 514/12; 514/210; 530/381
[58] Field of Search ..................... 530/381; 514/12, 514/21

[56] References Cited

U.S. PATENT DOCUMENTS 4,327,086  4/1982  Fukushima et al. ..................... 530/381
5,164,373  11/1992  Shikano et al. ..................... 514/12

OTHER PUBLICATIONS

Duckert, F., "Fibuiu Stabelizing Factor, Factor XIII", BLUT, 26(3)pp. 177–179 (1973) Abstract.

M. Mahi, "Hemostasis and Thrombosis in Obstetrics and Gynecology," Chapt 4, Die Medizinische Verlagsgellschaft mbH, (1991) pp. 78–92.

Schuling et al. "Fibrolinosys . . . Spont. Abortion Eur. J. Obstet. Gynecol Repnod Biol" (2–3) 1990 215–22 (abstract).

Adany & Muszbek, "Immunohistochemical Detection . . . in Human Uterus Histochemistry" '91 (2) 1989 pp. 169–174 (abstract).

Primary Examiner—Christina Y. Chan
Assistant Examiner—P. Lynn Touzean
Attorney, Agent, or Firm—Finnegan, Henderson, Farabow, Garrett & Dunner, L.L.P.

[57] ABSTRACT

Therapeutic agent for threatened abortion which contains human blood coagulation factor XIII as the active ingredient. Human blood coagulation factor XIII administered to patients with threatened abortion successfully treats the disease, and its effects are marked.

9 Claims, No Drawings

THERAPEUTIC AGENT FOR THREATENED ABORTION

This application is a continuation of application Ser. No. 08/026,010, filed Mar. 4, 1993, now abandoned.

This invention relates to an agent for treating threatened abortion.

Threatened abortion refers to a condition of a patient within 24 weeks of pregnancy, with an alive fetus, a slight uterine bleeding, parodynia-like pain, lumbago, and no dilatation of the cervix.

Since threatened abortion is a condition at the early stage of abortion, it may permit pregnancy to continue depending on treatment. If this condition proceeds, there will be no more recovery from it, and continuation of pregnancy will become impossible. Thus, treatment is required in order to return the patient promptly to the normal non-pregnant state.

The cause of threatened abortion is said to lie in the fetus and/or the mother. This condition due to the fetal cause can substantially be neither prevented nor treated. The maternal causes include genital inflammation, endocrine disorders, organic abnormalities of the uterus, infections, excessive labor or exercise, cardiac diseases, renal diseases, malnutrition, and psychophysical states. Usually, these causes are difficult to grasp clinically.

Current therapies for threatened abortion are rest and pharmacotherapies including luteal hormone and hCG, as well as hemostatics in the presence of uterine bleeding. None of these therapies have proved sufficiently effective.

It is the object of this invention to provide a therapeutic agent showing high efficacy against threatened abortion from the initial stage of treatment.

The present invention comprises a therapeutic agent for threatened abortion which contains human blood coagulation factor XIII (hereinafter referred to as factor XIII) as the active ingredient.

Factor XIII preparations are used mainly to treat disturbances in wound healing. We have now found that factor XIII exerts the action to ameliorate threatened abortion. This finding has led us to accomplishment of the invention.

Factor XIII is also called fibrin-stabilizing factor, fibrinase or plasma transglutaminase, the existence of which was suggested by Robbins in 1944. After studies by Laki and Lorand et al., factor XIII was adopted as its official name at the International Congress on Thrombosis and Haemostasis in 1963. It is widely distributed in plasma, placenta, etc. It acts as a transaminase, which is activated by thrombin and $Ca^{2+}$ and crosslinks fibrin molecules. The crosslinked molecules form a firm fibrin network that is stable to mechanical and chemical attacks. Besides this fibrin-stabilizing effect, factor XIII has also been demonstrated to play an important role in wound healing process by forming crosslinks between fibrin and fibronectin and promoting fibroblast proliferation and epidermis formation.

Factor XIII preparations have already been in wide use as therapeutic agents for wound healing disturbances, etc. Clinical experiences with their use in more than 10,000 patients at home and abroad have shown that these preparations are free from adverse or toxic reactions at a usual dose of about 20–50 units per kg body weight.

Factor XIII preparations are manufactured from human placentas or plasmas by well-known methods. An example of the manufacturing method using placentas is as follows:

Freeze placentas and divide them finely. Add an NaCl solution to the fine pieces, stir, and centrifuge to collect supernatant I. After ascertaining by enzyme immunoassay that this supernatant I is negative for HBs antigen, add a Rivanol solution to it and collect precipitate II that contains factor XIII. After washing the precipitate, add an NaCl solution containing EDTA to it and stir. Remove the insolubles (precipitate III) and obtain supernatant III. Then, add an N-cetylpyridinium chloride solution to supernatant III to precipitate contaminating proteins and mucopolysaccharides. Add a Rivanol solution to the supernatant IV so obtained, thereby generating precipitate V that contains factor XIII. Add an NaCl solution containing EDTA to this precipitate V, stir, and remove the insolubles (precipitate VI) to obtain supernatant VI. Add ammonium sulfate to supernatant VI to generate precipitate VII that contains factor XIII. Add an EDTA solution to precipitate VII and dialyze against a Tris-HCL buffer containing EDTA and sodium azide. After adjusting pH, remove precipitate VIII and subject supernatant VIII to gel filtration. Combine the active fractions and add ammonium sulfate to the combined fractions, thereby generating precipitate IX containing factor XIII. Dissolve this precipitate IX in a Tris-HCL buffer containing EDTA, dialyze against the same buffer, and adjust pH to collect a precipitate containing factor XIII in the form of euglobulin. Dissolve the euglobulin precipitate in an NaCl solution containing EDTA, and add aminoacetic acid and sucrose. Then, add ammonium sulfate to generate precipitate X containing factor XIII, dissolve this precipitate X in an NaCl solution containing EDTA, and dialyze against the same solution. Adjust the titer of factor XIII using an NaCl solution containing glucose and human serum albumin. Filter this solution aseptically, dispense into glass vials, and lyophilize.

In addition to the above-mentioned fractionation method, factor XIII can also be manufactured by genetic engineering. Factor XIII for use in this invention includes those produced by any possible methods, including fractionation and genetic engineering methods.

Since factor XIII manufactured by fractionation may possibly contain hepatitis viruses, AIDS virus, etc., it is desired to inactivate these viruses by heat treatment or any other means. The heat treatment is performed by dissolving factor XIII precipitated as euglobulin in an NaCl solution containing EDTA, and heating the solution at approximately 60° C. for 10 hours or so. Amino acids, e.g., glycine, saccharides, etc. can be used as stabilizers in the heat treatment.

The lyophilized factor XIII can directly be used as an injection by dissolving it in distilled water for injection (Japanese Pharmacopeia, JP) or the like just before use. The concentration of factor XIII in the injection should be about 250 units/4 ml. The injection can be given either intravenously or intramuscularly. No changes in the composition of the injection have been reported after the solution for injection is mixed with other agents. According to the general cautions for use, however, the injection of factor XIII mixed with other agents should be avoided.

Suitably, factor XIII should be administered by injection, but possible dosage forms include parenteral forms such as microcapsules and implants, oral forms such as liquids, tablets and capsules, and external forms such as ointments and suppositories.

Factor XIII is administered at a dose of about 1,500 units/day to a patient with threatened abortion. This therapy is continued until no extra-velamentum hematoma is detected in the patient. The usual duration of treatment is about 5 days. If any symptoms recur, treatment may be resumed at any time.

The present invention will be described in more detail with reference to Example of Formulation and Example of Clinical Trial using the therapeutic agent of the invention.

Example of Formulation

An aqueous solution of purified factor XIII adjusted to a concentration of 250 units/4 ml was charged into vials, and lyophilized to obtain the therapeutic agent of the invention. For use, this lyophilized factor XIII is dissolved in 4 ml distilled water for injection (JP) to make an injection.

Example of Clinical Trial

Subjects:

The subjects for a clinical trial were the following 4 patients with threatened abortion who were hospitalized at the Dept. of Obstetrics & Gynecology of "N" Hospital between March 1989 and October 1990 for atypical genital bleeding and lower abdominal pain, and whose ultrasound echograms showed a marked hematoma between the fetal membranes and the uterine wall.

TABLE 1

| Patient | Week of pregnancy at admission | Duration of treatment with FXIII | Week of pregnancy at delivery |
|---------|-------------------------------|----------------------------------|-------------------------------|
| A | W8&D3 | W10&D3-W11&D0 | W34&D2 |
| B | W12&D3 | W12&D6-W13&D3 | W40&D2 |
| C | W6&D0 | W8&D5-W9&D2 | W38&D3 |
| D | W11&D5 | W13&D0-W13&D4 | W39&D3 |

W = Week
D = Day

Results

The factor XIII levels in the 4 patients were all lower than 50% of the normal factor XIII range. After the factor XIII preparation of the invention was administered intravenously for 5 days at a daily dose of 1,500 units, the factor XIII levels increased to more than 80% of the normal range, and the extra-velamentum hematoma disappeared within one week. Then, pregnancy continued normally in all patients, and children were delivered normally with no influences from the disease.

Threatened abortion can be treated successfully with the factor XIII preparation of the invention. Its effects are much higher than those of conventional therapies.

We claim:

1. A method of treating threatened abortion which comprises administering to a patient in need thereof an effective amount of purified human blood coagulation factor XIII.

2. A method of treating threatened abortion as claimed in claim 1 comprising a route of administration selected from the group comprising injection, parenteral administration, microcapsules, implants, oral forms, liquids, tablets, capsules, external administration, ointments, and suppositories.

3. A method of treating threatened abortion as claimed in claim 1 comprising administration of approximately 1,500 units of human blood coagulation factor XIII a day for approximately 5 days.

4. A method of treating threatened abortion as claimed in claim 1 wherein the factor XIII is obtained from human placenta or plasma.

5. A method of treating threatened abortion as claimed in claim 1 wherein the factor XIII is obtained by manufacture using genetic engineering.

6. A method of treating threatened abortion as claimed in claim 1 wherein factor XIII is obtained by fractionation methods.

7. A method of treating threatened abortion as claimed in claim 1 wherein the factor XIII is treated before administration to remove any virus.

8. A method of treating threatened abortion as claimed in claim 7 wherein the factor XIII is treated by the steps comprising:

a) dissolving the precipitate factor containing factor XIII in the form of euglobulin in a NaCl solution containing EDTA, and b) allowing the solution to stand at approximately 600° C. for approximately 10 hours.

9. A method of treating threatened abortion as claimed in claim 8, wherein amino acids are used as stabilizers in the heat treatment.

* * * * *

UNITED STATES PATENT AND TRADEMARK OFFICE
CERTIFICATE OF CORRECTION

PATENT NO. : 5,554,593
DATED : September 10, 1996
INVENTOR(S) : Takayoshi NAKAYA et al It is certified that error appears in the above-indentified patent and that said Letters Patent is hereby corrected as shown below:

Claim 8, column 4, line 33, "600° C." should read --60° C.--.

Signed and Sealed this

Twenty-sixth Day of November 1996

BRUCE LEHMAN

Attest:

Attesting Officer        Commissioner of Patents and Trademarks